United States Patent [19]

Nakamura et al.

[11] Patent Number: 5,559,023
[45] Date of Patent: Sep. 24, 1996

[54] TUMOR SUPPRESSOR GENE

[75] Inventors: Yusuke Nakamura, Kanagawa; Takashi Imai, Chiba, both of Japan

[73] Assignees: Cancer Institute; Eisai Co., Ltd., both of Tokyo, Japan

[21] Appl. No.: 384,850

[22] Filed: Feb. 7, 1995

[30] Foreign Application Priority Data

Feb. 10, 1994 [JP] Japan ................. 6-037649

[51] Int. Cl.⁶ ............... C12N 5/10; C07H 21/04
[52] U.S. Cl. ................... 435/240.2; 536/23.5
[58] Field of Search .............. 536/23.5; 435/240.2

[56] References Cited

FOREIGN PATENT DOCUMENTS

84/03564  9/1984  WIPO .

OTHER PUBLICATIONS

Toda et al., "Isolation and Characterization of a Novel Gene Encoding Nuclear Protein at a Locus (D11S636) Tightly Linked to Multiple Endocrine Neoplasia Type 1 (MEN1)", Human Molecular Genetics, vol. 3, No. 3, pp. 465–470. Mar. 94.
Tanigami et al., "A 14–Mb Physical Map of the Region at Chromosome 11q13 Harboring the MEN1 Locus and the Tumor Amplicon Region", Genomics, vol. 13, No. 1, pp. 16–20. 1992.
S. H. Friend et al, Proc. Natl. Acad. Sci. USA, Dec. 1987, vol. 84, pp. 9059–9063.
D. P. Lane et al, Nature, 15 Mar. 1979, vol. 278, pp. 261–263.
K. W. Kinzler et al, Science, 9 Aug. 1991, vol. 253, pp. 661–665.
K. M. Call, et al, Cell, 9 Feb. 1990, vol. 60, pp. 509–520.
D. Malkin et al, Science, 30 Nov. 1990, vol. 250, pp. 1233–1238.
S. Srivastava et al, Nature, 20/27 Dec. 1990, vol. 348, pp. 747–749.
M. L. Brandi et al, Endocrine Reviews, Nov. 1987, vol. 8, No. 4, pp. 391–405.
E. Takahashi et al, Human Genetics, 15 Nov. 1989, vol. 86, pp. 14–16.
Y. Nakamura et al, Am. J. Hum. Genet., 1988, vol. 43, pp. 854–859.
A. J. Buckler, et al, Proc. Natl. Acad. Sci., May 1991, vol. 88, pp. 4005–4009.
A. M. Maxam et al, Proc. Natl. Acad. Sci., Feb. 1977, vol. 74, No. 2, pp. 560–564.
J. Messing et al, Nucleic Acids Research, 1981, vol. 9, No. 2, pp. 309–321.
A. Hinnen et al, Proc. Natl. Acad. Sci., Apr. 1978, vol. 75, No. 4, pp. 1929–1933.
C. Gorman et al, Science, 5 Aug. 1983, vol. 221, pp. 551–553.
A. Becker et al, Proc. Nat. Acad. Sci., Feb. 1975, vol. 72, No. 2, pp. 581–585.
C. Cepko et al, Cell, Jul. 1984, vol. 37, pp. 1053–1062.

T. Sato et al, Cancer Research, 15 Nov. 1990, vol. 50, pp. 7184–7189.
D. Wu et al, Genomics, 1989, vol. 4, pp. 560–569.
G. Ruano et al, Nucleic Acids Research, 1989, vol. 17, No. 20, pp. 8392–8393.
C. R. Newton et al, Nucleic Acids Research, 1989, vol. 17, No. 7, pp. 2503–2517.
M. Orita et al, Proc. Natl. Acad. Sci., Apr. 1989, vol. 86, pp. 2766–2770.
M. Orita et al., Genomics, 1989, vol. 5, pp. 874–879.
C. Larsson et al, Nature, 3 Mar. 1988, vol. 332, pp. 85–87.
Y. Nakamura et al, Am. J. Hum. Genet., 1989, vol. 44, pp. 751–755.
T. Tokino et al, Am. J. Hum. Genet., 1991, vol. 48, pp. 258–268.
A. Tanigami et al, Am. J. Hum. Genet., 1992, vol. 50, pp. 56–64.
T. Hori et al, Genomics, 1992, vol. 13, pp. 129–133.
M. Fujimori et al, Am. J. Hum. Genet., 1992, vol. 50, pp. 399–403.
E. Friedman et al, New England Journal of Medicine, 1989, vol. 321, No. 4, pp. 213–218.
R. Thakker et al, New England Journal of Medicine, 1989, vol. 321, No. 4, pp. 218–224.
A. Bale et al, Cancer Research, 15 Feb. 1991, vol. 51, pp. 1154–1157.
C. Bystrom et al, Proc. Natl. Acad. Sci., Mar. 1990, vol. 87, pp. 1968–1972.
A. Tanigami et al, Genomics, 1992, vol., 13, pp. 21–24.
M. Gessler et al, Nature, 22 Feb. 1990, vol. 343, pp. 774–778.
U. Rosenberg et al, Nature, 23 Jan. 1986, vol. 319, pp. 336–339.
P. Chavrier, et al, The EMBO Journal, 1988, vol. 7, No. 1, pp. 29–35.
L. Joseph et al, Proc. Natl. Acad. Sci., Oct. 1988, vol. 85, pp. 7164–7168.
J. Arriza et al, Science, 1987, vol. 237, pp. 268–275.
A. Krust et al, The EMBO Journal, 1986, vol. 5, No. 5, pp. 891–897.
V. Giguere et al, Cell, 29 Aug. 1986, vol. 46, pp. 645–652.

Primary Examiner—George C. Elliott
Attorney, Agent, or Firm—Flynn, Thiel, Boutell & Tanis, P.C.

[57] ABSTRACT

A detailed genetic map on human chromosome 11 was prepared. Then, a commonly deleted region on the chromosome in the tumor tissues of patients with multiple endocrine neoplasia type 1 was identified. Further, by linkage analysis of a family line with this disease, a genetic cause for this disease was localized. A gene present in the region common to these observations was cloned and the structure of this gene was determined. Because a protein coded by this DNA is homologous with those of transcriptional factors, it is expected that the above-mentioned gene may be a novel tumor suppressor gene. Further, it is also expected that the above-mentioned gene and a protein coded for thereby may be useful in preparation of a remedy for cancer and a diagnostic drug for cancer.

7 Claims, 4 Drawing Sheets

```
WT1  105 EASAERLQGRRSRG A--SGS EP QQ MGSDV RD LNA LL PA VPSLGGGGCA LP VS G AAQW-160
ZFM1 393 GPHSF PHPL PSLTGG--H GG HPM Q       PWMQPPP PP PMNQG PH- PPGHHGP PPM-447
EGR2 166 SPPP PPPP PPYSGCAGDLYQDPSAFLS AATTSTSSSLAYPPPS YP SPK- P ATDPG LFPM-223

WT1  161 APVLD FAP PGAS-AY--GSL GG PA- PP PAPPP PP HSF I KQ EP SWGGAEP-HE EQ 213
ZFM1 448 DQYLGSTPVGSG-VYRLHQGKGMMP- PPP MGMMP- PPP PPP PSG-Q PP PSGPLP PWQQQ 503
EGR2 224 PDYPGFFPSQCQRDLHGTAGPDRKPF CPLDTLRVPPLTPL-STIRNFTLGGPSAGMT 278
```

FIG. 4

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 3200 base pairs
        ( B ) TYPE: nucleic acid
        ( C ) STRANDEDNESS: double
        ( D ) TOPOLOGY: linear     ( i i ) MOLECULE TYPE: cDNA     ( v i ) ORIGINAL SOURCE:
        ( A ) ORGANISM: Homo sapiens     ( i x ) FEATURE:
        ( A ) NAME/KEY: 5'UTR
        ( B ) LOCATION: 1..382
        ( A ) NAME/KEY: CDS
        ( B ) LOCATION: 383..2254
        ( A ) NAME/KEY: exon 1
        ( B ) LOCATION: 1..413
        ( A ) NAME/KEY: exon 2
        ( B ) LOCATION: 414..542
        ( A ) NAME/KEY: exon 3
        ( B ) LOCATION: 543..618
        ( A ) NAME/KEY: exon 4
        ( B ) LOCATION: 619..771
        ( A ) NAME/KEY: exon 5
        ( B ) LOCATION: 772..861
        ( A ) NAME/KEY: exon 6
        ( B ) LOCATION: 862..1045
        ( A ) NAME/KEY: exon 7
        ( B ) LOCATION: 1046..1161
        ( A ) NAME/KEY: exon 8
        ( B ) LOCATION: 1162..1269
        ( A ) NAME/KEY: exon 9
        ( B ) LOCATION: 1270..1450
        ( A ) NAME/KEY: exon 10
        ( B ) LOCATION: 1451..1724
        ( A ) NAME/KEY: exon 11
        ( B ) LOCATION: 1725..1784
        ( A ) NAME/KEY: exon 12
        ( B ) LOCATION: 1785..1964
        ( A ) NAME/KEY: exon 13
        ( B ) LOCATION: 1965..2137
        ( A ) NAME/KEY: exon 14
        ( B ) LOCATION: 2138..3132
        ( A ) NAME/KEY: 3'UTR
        ( B ) LOCATION: 2280..3200

( x i ) SEQUENCE DESCRIPTION: SEQ ID NO:1:

```
CGTTGCTGTC GAAATGAAGT GCGCGCTGCG ACACCTCCCA GCCCACCGAA CTCCGCCGCC      60

ATTTCCTCGC TTGCCTAACG GTTCGGCCAA TCCCAGCGCG CATCAATGCC GGACTGAGGC     120

TCCGCCAATC GGAGGCCGCC GATTTCGACC CTTCGCCTCG GCCCGGCCCA ATCCATTCCC     180

CGGCCCCGCC GCCCCCGGCC CGCCCCCGCG GTGCCCTCTC TCCTCCCTCT TTGTGCGTCT     240

CGCGCCGCCG CCGCCCGCCG CGTGAGAGGA CGGGCTCCGC GCGCTCCGGC AGCGCATTCG     300

GGTCCCCTCC CCCCGGGAGG CTTGCGAAGG AGAAGCCGCC GCAGAGGAAA AGCAGGTGCC     360

GGTGCCTGTC CCCGGGGGCG CC ATG GCG ACC GGA GCG AAC GCC ACG CCG TTG     412
                        Met Ala Thr Gly Ala Asn Ala Thr Pro Leu
                         1               5                    10

GAC TTC CCA AGT AAG AAG CGG AAG AGG AGC CGC TGG AAC CAA GAC ACA      460
Asp Phe Pro Ser Lys Lys Arg Lys Arg Ser Arg Trp Asn Gln Asp Thr
             15                  20                  25

ATG GAA CAG CCG ACA GTG ATT CCA GGA ATG CCT ACA GTT ATT CCC CCT      508
```

-continued

| | | | | | | | | | | | | | | | | |
|---|---|---|---|---|---|---|---|---|---|---|---|---|---|---|---|---|
| Met | Glu | Gln | Pro | Thr | Val | Ile | Pro | Gly | Met | Pro | Thr | Val | Ile | Pro | Pro | |
| | | | 30 | | | | | 35 | | | | | 40 | | | |
| GGA | CTT | ACT | CGA | GAA | CAA | GAA | AGA | GCT | TAT | ATA | GTG | CAA | CTG | CAG | ATA | 556 |
| Gly | Leu | Thr | Arg | Glu | Gln | Glu | Arg | Ala | Tyr | Ile | Val | Gln | Leu | Gln | Ile | |
| | | 45 | | | | | 50 | | | | | 55 | | | | |
| GAA | GAC | CTG | ACT | CGT | AAA | CTG | CGC | ACA | GGG | GAC | CTG | GGC | ATC | CCC | CCT | 604 |
| Glu | Asp | Leu | Thr | Arg | Lys | Leu | Arg | Thr | Gly | Asp | Leu | Gly | Ile | Pro | Pro | |
| | | | 60 | | | | | 65 | | | | | 70 | | | |
| AAC | CCT | GAG | GAC | AGG | TCC | CCT | TCC | CCT | GAG | CCC | ATC | TAC | AAT | AGC | GAG | 652 |
| Asn | Pro | Glu | Asp | Arg | Ser | Pro | Ser | Pro | Glu | Pro | Ile | Tyr | Asn | Ser | Glu | |
| 75 | | | | | 80 | | | | | 85 | | | | | 90 | |
| GGG | AAG | CGG | CTT | AAC | ACC | CGA | GAG | TTC | CGC | ACC | CGC | AAA | AAG | CTG | GAA | 700 |
| Gly | Lys | Arg | Leu | Asn | Thr | Arg | Glu | Phe | Arg | Thr | Arg | Lys | Lys | Leu | Glu | |
| | | | | 95 | | | | | 100 | | | | | 105 | | |
| GAG | GAG | CGG | CAC | AAC | CTC | ATC | ACA | GAG | ATG | GTT | GCA | CTC | AAT | CCG | GAT | 748 |
| Glu | Glu | Arg | His | Asn | Leu | Ile | Thr | Glu | Met | Val | Ala | Leu | Asn | Pro | Asp | |
| | | | 110 | | | | | 115 | | | | | 120 | | | |
| TTC | AAG | CCA | CCT | GCA | GAT | TAC | AAA | CCT | CCA | GCA | ACA | CGT | GTG | AGT | GAT | 796 |
| Phe | Lys | Pro | Pro | Ala | Asp | Tyr | Lys | Pro | Pro | Ala | Thr | Arg | Val | Ser | Asp | |
| | | 125 | | | | | 130 | | | | | 135 | | | | |
| AAA | GTC | ATG | ATT | CCA | CAA | GAT | GAG | TAC | CCA | GAA | ATC | AAC | TTT | GTG | GGG | 844 |
| Lys | Val | Met | Ile | Pro | Gln | Asp | Glu | Tyr | Pro | Glu | Ile | Asn | Phe | Val | Gly | |
| | 140 | | | | | 145 | | | | | 150 | | | | | |
| CTG | CTC | ATC | GGG | CCC | AGA | GGG | AAC | ACC | CTG | AAG | AAC | ATA | GAG | AAG | GAG | 892 |
| Leu | Leu | Ile | Gly | Pro | Arg | Gly | Asn | Thr | Leu | Lys | Asn | Ile | Glu | Lys | Glu | |
| 155 | | | | | 160 | | | | | 165 | | | | | 170 | |
| TGC | AAT | GCC | AAG | ATT | ATG | ATC | CGG | GGG | AAA | GGG | TCT | GTG | AAA | GAA | GGG | 940 |
| Cys | Asn | Ala | Lys | Ile | Met | Ile | Arg | Gly | Lys | Gly | Ser | Val | Lys | Glu | Gly | |
| | | | | 175 | | | | | 180 | | | | | 185 | | |
| AAG | GTT | GGG | CGC | AAA | GAT | GGC | CAG | ATG | TTG | CCA | GGA | GAA | GAT | GAG | CCA | 988 |
| Lys | Val | Gly | Arg | Lys | Asp | Gly | Gln | Met | Leu | Pro | Gly | Glu | Asp | Glu | Pro | |
| | | | 190 | | | | | 195 | | | | | 200 | | | |
| CTT | CAT | GCC | CTG | GTT | ACT | GCC | AAT | ACA | ATG | GAG | AAC | GTC | AAA | AAG | GCA | 1036 |
| Leu | His | Ala | Leu | Val | Thr | Ala | Asn | Thr | Met | Glu | Asn | Val | Lys | Lys | Ala | |
| | | 205 | | | | | 210 | | | | | 215 | | | | |
| GTG | GAA | CAG | ATA | AGA | AAC | ATC | CTG | AAG | CAG | GGT | ATC | GAG | ACT | CCA | GAG | 1084 |
| Val | Glu | Gln | Ile | Arg | Asn | Ile | Leu | Lys | Gln | Gly | Ile | Glu | Thr | Pro | Glu | |
| | 220 | | | | | 225 | | | | | 230 | | | | | |
| GAC | CAG | AAT | GAT | CTA | CGG | AAG | ATG | CAG | CTT | CGG | GAG | TTG | GCT | CGC | TTA | 1132 |
| Asp | Gln | Asn | Asp | Leu | Arg | Lys | Met | Gln | Leu | Arg | Glu | Leu | Ala | Arg | Leu | |
| 235 | | | | | 240 | | | | | 245 | | | | | 250 | |
| AAT | GGG | ACC | CTT | CGG | GAA | GAC | GAT | AAC | AGG | ATC | TTA | AGA | CCC | TGG | CAG | 1180 |
| Asn | Gly | Thr | Leu | Arg | Glu | Asp | Asp | Asn | Arg | Ile | Leu | Arg | Pro | Trp | Gln | |
| | | | | 255 | | | | | 260 | | | | | 265 | | |
| AGC | TCA | GGG | ACC | CGC | AGC | ATT | ACC | AAC | ACC | ACA | GTG | TGT | ACC | AAG | TGT | 1228 |
| Ser | Ser | Gly | Thr | Arg | Ser | Ile | Thr | Asn | Thr | Thr | Val | Cys | Thr | Lys | Cys | |
| | | | 270 | | | | | 275 | | | | | 280 | | | |
| GGA | GGG | GCT | GGC | CAC | ATT | GCT | TCA | GAC | TGT | AAA | TTC | CAA | AGG | CCT | GGT | 1276 |
| Gly | Gly | Ala | Gly | His | Ile | Ala | Ser | Asp | Cys | Lys | Phe | Gln | Arg | Pro | Gly | |
| | | | 285 | | | | | 290 | | | | | 295 | | | |
| GAT | CCT | CAG | TCA | GCT | CAG | GAT | AAA | GCA | CGG | ATG | GAT | AAA | GAA | TAT | TTG | 1324 |
| Asp | Pro | Gln | Ser | Ala | Gln | Asp | Lys | Ala | Arg | Met | Asp | Lys | Glu | Tyr | Leu | |
| | | 300 | | | | | 305 | | | | | 310 | | | | |
| TCC | CTC | ATG | GCT | GAA | CTG | GGT | GAA | GCA | CCT | GTC | CCA | GCA | TCT | GTG | GGC | 1372 |
| Ser | Leu | Met | Ala | Glu | Leu | Gly | Glu | Ala | Pro | Val | Pro | Ala | Ser | Val | Gly | |
| 315 | | | | | 320 | | | | | 325 | | | | | 330 | |
| TCC | ACC | TCT | GGG | CCT | GCC | ACC | ACA | CCC | CTG | GCC | AGC | GCA | CCT | CGT | CCT | 1420 |
| Ser | Thr | Ser | Gly | Pro | Ala | Thr | Thr | Pro | Leu | Ala | Ser | Ala | Pro | Arg | Pro | |
| | | | 335 | | | | | 340 | | | | | 345 | | | |
| GCT | GCT | CCC | GCC | AAC | AAC | CCA | CCT | CCA | CCG | TCT | CTC | ATG | TCT | ACC | ACC | 1468 |

| | | | | | | | | | | | | | | | | |
|---|---|---|---|---|---|---|---|---|---|---|---|---|---|---|---|---|
| Ala | Ala | Pro | Ala 350 | Asn | Asn | Pro | Pro 355 | Pro | Pro | Ser | Leu | Met | Ser 360 | Thr | Thr | |
| CAG Gln | AGC Ser | CGC Arg 365 | CCA Pro | CCC Pro | TGG Trp | ATG Met | AAT Asn 370 | TCT Ser | GGT Gly | CCT Pro | TCA Ser | GAG Glu | AGT Ser 375 | TGG Trp | CCC Pro | 1516 |
| TAC Tyr | CAC His 380 | GGC Gly | ATG Met | CAT His | GGA Gly | GGT Gly 385 | GGT Gly | CCT Pro | GGT Gly | GGG Gly | CCA Pro 390 | GGA Gly | GGT Gly | GGC Gly | CCC Pro | 1564 |
| CAC His 395 | AGC Ser | TTC Phe | CCA Pro | CAC His | CCA Pro 400 | TTA Leu | CCC Pro | AGC Ser | CTG Leu | ACA Thr 405 | GGT Gly | GGG Gly | CAT His | GGT Gly | GGA Gly 410 | 1612 |
| CAT His | CCC Pro | ATG Met | CAG Gln | CAC His 415 | AAC Asn | CCC Pro | AAT Asn | GGA Gly 420 | CCC Pro | CCA Pro | CCC Pro | CCT Pro | TGG Trp 425 | ATG Met | CAG Gln | 1660 |
| CCA Pro | CCA Pro | CCA Pro | CCA Pro 430 | CCG Pro | ATG Met | AAC Asn | CAG Gln | GGC Gly 435 | CCC Pro | CAC His | CCT Pro | CCT Pro | GGG Gly 440 | CAC His | CAT His | 1708 |
| GGC Gly | CCT Pro | CCT Pro 445 | CCA Pro | ATG Met | GAT Asp | CAG Gln | TAC Tyr 450 | CTG Leu | GGA Gly | AGT Ser | ACG Thr | CCT Pro 455 | GTG Val | GGC Gly | TCT Ser | 1756 |
| GGG Gly | GTC Val 460 | TAT Tyr | CGC Arg | CTG Leu | CAT His | CAA Gln 465 | GGA Gly | AAA Lys | GGT Gly | ATG Met | ATG Met 470 | CCG Pro | CCA Pro | CCA Pro | CCT Pro | 1804 |
| ATG Met 475 | GGC Gly | ATG Met | ATG Met | CCG Pro 480 | CCG Pro | CCG Pro | CCG Pro | CCG Pro | CCT Pro | CCC Pro 485 | AGT Ser | GGG Gly | CAG Gln | CCC Pro | CCA Pro 490 | 1852 |
| CCC Pro | CCT Pro | CCC Pro | TCT Ser | GGT Gly 495 | CCT Pro | CTT Leu | CCC Pro | CCA Pro | TGG Trp 500 | CAA Gln | CAA Gln | CAG Gln | CAG Gln | CAG Gln 505 | CAG Gln | 1900 |
| CCT Pro | CCG Pro | CCA Pro | CCC Pro 510 | CCT Pro | CCG Pro | CCC Pro | AGC Ser | AGC Ser 515 | AGT Ser | ATG Met | GCT Ala | TCC Ser | AGT Ser 520 | ACC Thr | CCC Pro | 1948 |
| TTG Leu | CCA Pro | TGG Trp 525 | CAG Gln | CAA Gln | AAT Asn | ACG Thr | ACG Thr 530 | ACT Thr | ACC Thr | ACC Thr | ACG Thr | AGC Ser 535 | GCT Ala | GGC Gly | ACA Thr | 1996 |
| GGG Gly | TCC Ser 540 | ATC Ile | CCG Pro | CCA Pro | TGG Trp | CAA Gln 545 | CAG Gln | CAG Gln | CAG Gln | GCG Ala | GCT Ala 550 | GCC Ala | GCA Ala | GCT Ala | TCT Ser | 2044 |
| CCA Pro 555 | GGA Gly | GCC Ala | CCT Pro | CAG Gln | ATG Met 560 | CAA Gln | GGC Gly | AAC Asn | CCC Pro | ACT Thr 565 | ATG Met | GTG Val | CCC Pro | CTG Leu | CCC Pro 570 | 2092 |
| CCC Pro | GGG Gly | GTC Val | CAG Gln | CCG Pro 575 | CCT Pro | CTG Leu | CCG Pro | CCT Pro | GGG Gly 580 | GCC Ala | CCT Pro | CCC Pro | CCT Pro | CCG Pro 585 | CCC Pro | 2140 |
| CGT Arg | AGC Ser | ATC Ile | GAG Glu 590 | TGT Cys | CTT Leu | CTT Leu | TGT Cys | CTT Leu 595 | CTT Leu | TCT Ser | CTC Leu | CTC Leu | ACC Thr 600 | CAA Gln | CTC Leu | 2188 |
| CCT Pro | TTG Leu | CCT Pro 605 | CTC Leu | CCC Pro | AAA Lys | CCG Pro | GGC Gly 610 | CGC Arg | CAG Gln | GAT Asp | CCC Pro | TCC Ser 615 | CCG Pro | CGG Arg | CGG Arg | 2236 |
| CGA Arg | TGG Trp | CCC Pro 620 | GAG Glu | CCA Pro 623 | TGAGAGTGAG | | GACTTTCCGC | | GCCCATTGGT | | GACCCTTCCA | | | | | 2291 |

GGCAGACAGC CTCAGCAACG CCCCTGGTGG ACAGGATGGT TCGGCAAAGC AGCCTGAGTT 2351

ATTTTTGTGG ACGGAATCGG AACACGCTGG CTCCATATCG TGAAATTTTT ATTAATTTTT 2411

TTCTTTTTCC TTTGTTACTT CTTTATCTTT TCCTTTCTTC AGACTCCGTC CAAGGAGATG 2471

CTCTCCCCGG TCTTCTGCTG CAATTTAGAT TCCTTTGGGT TCTCTCCAGT TCTCCTTCCC 2531

TTACCAAGGA GAGGGGAGCA AATGGTTTTG GGCAAGGGCT TTGGCCATTC ATGTCAAGCT 2591

```
GGTTGTGGGT  TTTTCAAGGT  GCCATAGCCA  CCCCCAAATA  TGTTTGTTTA  AAGCGTGGGG  2651

TTTTTTAATC  TCTGCCACCC  TTGTCAAGGG  AGTCTTGTAA  AGTTGCCGAG  GGTAGGTTCA  2711

TCTCCAGGTT  TCGGGATTCC  CATCCGTCCT  GGCGATCCTG  CCAGCAGTGG  GTGGGCAGCC  2771

TGAGCTCCCT  CGGGCTCGCC  TGCCAGCCTG  GAGTTCTTCC  TGTGCTCCTT  GATCACCTGA  2831

GCTGCCTCAG  ATTCCATTTG  GTCCTCTCCT  TCCTGGAAGG  CTTCCTTTTA  TGTTTTGTTT  2891

TAATCCCAAA  TGTCTGAATG  TTTTGCAGTG  TGTAGGGGTT  TGAGCCCCTT  GTTCATTCTC  2951

CTTCCTTTTT  CCTCCCGCTT  CCCTCTCCAT  GAAGTGATTC  TGTTGACAAT  AATGTATACT  3011

GCGCGTTCTC  TTCACTGGTT  TATCTGCAGA  AATTTCTCTG  GGCTTTTTTC  GGTGTTAGAT  3071

TCAACACTGC  GCTAAAGCGG  GGATGTTCCA  TTGAATAAAA  GAGCAGTGTG  GTTTCTGGG   3131

AAAAAAAAAA  AAAAAAAAAA  AAAAAAAAAA  AAAAAAAAAA  AAAAAAAAAA  AAAAAAAAAA  3191

AAAAAAAA                                                                3200
```

TUMOR SUPPRESSOR GENE

BACKGROUND OF THE INVENTION

1. Field of the Invention

The present invention relates to a human tumor suppressor gene, a polypeptide coded for thereby and a gene analysis method wherein the above-mentioned gene is used. Thus, they are usable in the field of medicines.

2. Description of the Related Art

It has been known for a long time that genetic mutation in cells plays an important role in the onset of cancer. Recent advances in genetic engineering have made it possible to amplify specific DNAs and to analyze gene mutations in cancer cells and thus contributed to the remarkable development in the field of studies on cancer.

Analysis and identification of oncogenes, which are thought to participate in the cancerization of cells and the abnormal proliferation of cancer cells, are now in progress and the number of the oncogenes thus clarified so far amounts to several score. On the other hand, tumor suppressor genes having a reverse function have been the focus of intense research interest in these several years. Examples of the tumor suppressor genes which have been found so far include Rb gene of retinoblastoma [Friend, S. H., et al., Proc. Natl. Acad. Sci. USA., 84, 9095 (1987)], p53 gene [Lane, D. P., et al., Nature, 278, 261 (1979)] and APC gene [Kenneth, W. K., et al., Science, 253, 661 (1991)] of colon cancer and WT1 gene of Wilms' tumor [Call, K. M., et al., Cell, 60, 509 (1990)]. In the case of the p53 gene, it is known that this mutation gene has been handed down over generations as a germ-line in certain family lines ["Li-Fraumeni syndrome"; Makin, D., et al., Science, 250, 1233 (1990); and Srivastava, S., et al., Nature, 348, 747 (1990)]. However, it is considered that there are many more unidentified tumor suppressor genes.

Multiple endocrine neoplasia type 1 (MEN1) is an autosomal dominant hereditary disease characterized by the development of hyperplasia or neoplasm in the endocrine organs such as accessory thyroid, islets of Langerhans in the pancreas and pituitary gland [Brandi, M. L., et. al., Endocr. Rev. 8, 391 (1987)]. It is assumed by linkage studies that a genetic defect exists in the long arm of chromosome 11 (11q). Also there is known a region which is deleted with high frequency on chromosome 11q in MEN 1-associated tumors. Based on these facts, it is considered that a tumor suppressor gene exists in this region.

Accordingly, it is now the focus of world-wide interest of physicians and researches to isolate this tumor suppressor gene, to clarify its role in the disease and to clarify its biological function. Thus it has been urgently required to isolate the tumor suppressor gene in this region.

It is an object of the present invention to provide a novel tumor suppressor gene, a transformant transformed by a plasmid having, integrated therein, the full structure or part of the tumor suppressor gene, a polypeptide which is coded for by the tumor suppressor gene, an antibody against the polypeptide and methods for studying, examining, diagnosing and medically treating cancer with the use of them.

DISCLOSURE OF THE INVENTION

SUMMARY OF THE INVENTION

The present inventors isolated cosmid clones containing a number of RFLP markers on chromosome 11 and prepared a detailed genetic map. By using these newly developed RFLP markers, a region deleted commonly in such tumors was further localized. And, a region where the target tumor suppressor gene existed was restricted to through the linkage analysis. As a result, the region common to these observations was specified as 11q13. From among cosmid clones of this region, those containing exons were selected. By using a fragment thereof as a probe, a cDNA library was screened. Thus a cDNA coding for an amino acid sequence beng homologous with transcriptional factors such as human Wilms' tumor suppressor gene (WT1) product and human early growth response protein 2 (EGR2) was isolated.

An organism specifically responds to various exogenous and endogenous stimuli by comprehensively utilizing, for example, its nervous, immune, circulatory and endocrine systems. After being input, information is transmitted via the so-called information transmitting system or enters directly into nuclei and thus acts on a gent or a transcriptional factor. As a result, the expression of the gent is modified and thus cells begin to take a turn for the differentiation, proliferation (cancerization) or death. From the very beginning, the process of the ontogeny and morphogenesis of an organism or the sustenance of its life per se is merely the results of the cascade mechanism of gene expression. Thus, it is not too much to say that nothing but "the coordination in gene expression depending mainly on transcription" makes a living organism as it is and cancer breaks out when this coordination falls into disorder.

Therefore, we deemed the clone thus isolated as one of tumor suppressor genes, isolated the cDNA thereof in the full length and analyzed the structure thereof. As a result, it has been proved that a protein which is coded for by this cDNA in the full length is an intranuclear transcriptional regulator having a nuclear localizing signal, a proline-rich domain and a zinc finger motif.

Thus, the present invention relates to:

(1) a DNA comprising the full structure or a part of the DNA represented by SEQ ID NO:1;

(2) a polypeptide comprising the full structure or a part of the polypeptide coded for by the DNA represented by SEQ ID NO:1;

(3) a transformant transformed by a plasmid having, integrated therein, the full structure or a part of the DNA represented by SEQ ID NO:1 which can be expressed therein;

(4) an antibody against the above-mentioned polypeptide as an antigen; and (5) a gene analysis method which comprises using, as a primer, a probe or a marker, a DNA comprising a part of the DNA represented by SEQ ID NO:1 and hybridizing the primer, the probe or the marker with a DNA to be tested.

In other words, the present invention relates to:

(a) a cDNA which comprises one containing the full or a part of the cDNA of the tumor suppressor gene represented by SEQ ID NO:1;

(b) a polypeptide which comprises one containing the full or a part of the polypeptide coded for by the cDNA of the tumor suppressor gone represented by SEQ ID NO:1;

(c) host cells which are obtained by integrating the full or a part of the cDNA described in SEQ ID NO:1 into a plasmid which can express it and transforming the cell thereby;

(d) an antibody against the polypeptide described in the above item (b) as an antigen; and (e) a gene analysis method characterized by using a DNA containing a part of the DNA sequence described in the above item (a) as a primer, a probe or a marker.

With respect to the DNAs and polypeptides, those which are substantially equivalent to the DNAs and polypeptides described above are also included in the scope of the present invention. The expression "DNAs and polypeptides being substantially equivalent" means those which have been modified via, for example, deletion, replacement, addition or insertion of the constituting bases or constituting amino acids and derivatives thereof, which exhibit the same effects as those of the original DNAs or polypeptides. However, the extent of these effects is irrelevant thereto. The term "a part of the DNA" means a fragment composed of at least 10 bases derived from the DNA. In order to employ as a primer, for example, a DNA fragment having a base sequence generally consisting of 10 to 30 bases, preferably 15 to 25 bases, is selected. In order to employ as a probe, a DNA fragment having a base sequence generally consisting of at least 15 bases, preferably at least 20 bases, is selected.

The term "a part of the polypeptide" means a peptide having a sequence composed of at least 6 amino acid residues derived from the polypeptide. When a part of a polypeptide is to be used as an antigen for the preparation of an antibody or as an epitope for the detection of an antibody, it is known that a peptide having a sequence consisting of 6 amino acid residues would bind to an antibody [see WO 8403564, published on Sep. 13, 1984 (Assignee: COMMONWEALTH SERUM LABS and GEYSEN, H. M.)]. A peptide having a sequence generally consisting of at least 10 amino acid residues, preferably at least 20 amino acid residues, is employed therefor. Although it may be anticipated that a peptide having a sequence consisting of 6 amino acid residues can achieve only a poor efficiency in the production of an antibody, such a peptide is also usable in the form of a fused peptide.

Furthermore, an RNA which comprises one translated from the DNA represented by SEQ ID NO:1 or a part of the same and RNAs which are substantially equivalent thereto are included in the scope of the present invention.

Now the present invention will be described in greater detail.

DETAILED DESCRIPTION OF THE INVENTION (1) Isolation of cDNA

The target cosmid library of the human chromosome 11 can be prepared in, for example, the following manner. From a human/mouse hybrid cell line containing a single human chromosome 11 in a mouse genomic background, a chromosomal DNA is extracted. Then DNA fragments of the chromosomal DNA can be integrated into a vector such as pWE15 by a conventional method [Maniatis, T., et al., Molecular Cloning 2nd. ed., Cold Spring Harbor Laboratory Press, N.Y. (1989)]. Clones having an insert originating in the human chromosome can be screened by colony hybridization with the use of a whole human DNA as a probe. The thus obtained cosmid clones containing a DNA originating in the human chromosome 11 are then subjected to the fluorescent in-situ hybridization (FISH) method [Takahashi et al., Am. J. Hum. Genet., 86, 14–16 (1990)]. Thus, each of the multitude of the cosmid clones can be localized throughout the chromosome and a physical chromosomal map can be prepared. Further, RFLP markers can be isolated on the basis of the fragment length pattern which has been prepared by cleaving human DNA with several restriction enzymes [Nakamura et al., Am. J. Hum. Genet., 43, 854–859 (1988)].

Among these clones, those located around the region of 11q13 are subjected to FISH method and the linkage analysis to thereby give a further detailed genetic map. Based on this map, the DNA of a cancer tissue of a patient is examined in the loss of heterozygosity (LOH) by utilizing the RFLP. Thus, the region where the target tumor suppressor gene is located can be further restricted to.

From the cosmid clones existing in the region which has been thus restricted to, a DNA fragment being expressed can be isolated by the exon trapping method [Buckler, A., et al., Proc. Natl. Acad. Sci. USA, 88, 4005–4009 (1991)]. By using the DNA fragment thus obtained as a probe, the cDNA of a gene existing in the restricted region near q13 of human chromosome 11 can be cloned.

(2) Confirmation of the whole structure of the gene

The base sequence of the cDNA can be determined by the Maxam-Gilbert method [Maxam, A. M. and Gilbert, W., Proc. Natl. Acad. Sci. USA, 74, 560 (1977)] or the dideoxy technique [Messing, J., Nucleic acid Res., 9, 309 (1981)].

It can be confirmed by, for example, the 5'RACE method, the 3'RACE method or the Northern blotting method, that the cDNA obtained by the above-mentioned method contains the full length protein translation region.

(3) Recombinant expression vectors and transformants transformed thereby

The tumor suppressor gene cDNA obtained by the above-mentioned method, or a fragment thereof, is integrated into an appropriate vector and then this vector is introduced into appropriate host cells to obtain a transformant. By culturing this transformant in a conventional manner, a large amount of the tumor suppressor gene product, or a fragment thereof can be obtained from the culture. More specifically, the cDNA is linked to the downstream side of the promoter of a vector suitable for the expression of the cDNA by a known method with the use of restriction enzymes and DNA ligase. Thus, a recombinant expression vector can be constructed. Examples of the vectors usable therefor include plasmids pRB322 and pUC18 originating in *Escherichia coli*, plasmid pUB110 originating in *Bacillus subtilis*, plasmid pRB15 originating in yeast, phage vectors λgt10 and λgt11, and vector SV40 originating in animal virus, though any vector capable of replicating and amplifying in the host cells may be used therefor without restriction. Similarly the promoter and the terminator are not restricted in particular and any suitable combination may be selected therefor depending on the host to be used, so long as they are adapted for the host employed in the expression of a DNA sequence coding for the tumor suppressor gene, or a fragment thereof. Any DNA may be used as the cDNA herein so long as it codes for the tumor suppressor gene product, or a fragment thereof. A chemically synthesized one may be used therefor. When the protein to be expressed is one having a physiological activity of suppressing the proliferation of cancer cells, then the sequence of the cDNA is not restricted to the DNA sequence represented by the SEQ ID NO:1 but a DNA having a DNA sequence which has undergone partial substitution, deletion, insertion or a combination thereof may be used therefor as the cDNA.

The recombinant expression vector thus obtained is introduced into a host by, for example, the competent cell method [J. Mol. Biol., 53, 154 (1970)], the protoplast method [Proc. Natl. Aced. Sci. USA, 75, 1929 (1978)], the calcium phosphate method [Science, 221, 551 (1988)], the in vitro packaging method [Proc. Natl. Acad. Sci. USA, 72, 581 (1975)] or the virus vector method [Cell, 37, 1053 (1984)] to thereby prepare a transformant. *Escherichia coli, Bacillus subtilis,* yeasts and animal cells are usable as the host. The transformant thus obtained is then cultured in an appropriate medium selected depending on the employed host. The culturing is usually effected at a temperature of from 20° to 45° C. within a pit range of from 5 to 8 and, if necessary, under aeration and/or stirring. The tumor suppressor gene product or a fragment thereof may be separated and purified from the culture by appropriately combining known separation/isolation methods. Examples of these methods include salting out, solvent precipitation, dialysis, gel filtration, electrophoresis, ion exchange chromatography, affinity chromatography and reversed phase high performance liquid chromatography.

(4) Preparation of antibody

By using the tumor suppressor gene product or a fragment thereof as an antigen, an antibody is prepared. A polyclonal antibody is prepared in accordance with a conventional method by, for example, sufficiently immunizing an animal such as mouse, guinea pig and rabbit with the antigen by subcutaneously, intramuscularly, intraperitoneally or intravenously administering it a number of times, sampling the blood from the animal and then separating the serum to obtain the antibody. A commercially available adjuvant is also usable therefor.

A monoclonal antibody can be prepared by a known method. For example, spleen cells of a mouse immunized with the antigen described above are fused with commercially available mouse myeloma cells to thereby give hybridomas. Then the target monoclonal antibody can be prepared from the culture supernatant of the hybridoma or the ascites fluid of a mouse inoculated with the hybridoma.

It is not necessary that the tumor suppressor gene product to be used as the antigen has the whole amino acid structure but a peptide having a partial structure thereof, a modified peptide, its derivative or a fused peptide formed by fusing this peptide with another peptide are also usable. These substances may be prepared by any of the biological technique and chemical synthesis technique.

These antibodies enable the identification and determination of the peptide of the present invention in human biological samples and thus are applicable to, for example, diagnostic drugs for diseases to which the polypeptide is related. The peptide can be immunologically assayed in accordance with any of the known methods including the fluorescent antibody method, the passive agglutination method and the enzyme-labeled antibody technique.

(5) Gene analysis of human organic tissues

Examples of the biological sample usable in the gene analysis include normal human tissues, various types of human tumor tissues, human blood, human bodily fluids and human secretions. The DNA of the employed tissue may be extracted and prepared by, for example, the method reported by Sato, T., et al. [Cancer Res., 50, 7184 (1990)].

From the DNA sequence provided by the present invention, a partial DNA sequence at an appropriate position is selected and a synthetic oligonucleotide having this sequence or one complementary thereto is used as a primer, a probe or a marker. Thus, the occurrence of a mutation of this gene in man and the morphology of the mutation can be analyzed. Furthermore, alterations (insertions, deletions, etc.) of this gene in a sample can also be detected by these analyses.

The part DNA sequence may be selected from any part of the DNA sequence of the above-mentioned gene. It is needless to say that an artificially modified DNA sequence may be used therefor and, thus, the corresponding gene mutation can be detected.

The analysis may be effected by, for example, the following method. Namely, primers of two sequences are selected and the partial sequence between them is amplified by the PCR method. Then, the amplified DNA sequence is directly analyzed. Alternatively, this amplification product is integrated into a plasmid in the same manner as that of the above-mentioned case and host cells are transformed thereby. After culturing the transformant thus obtained, the DNA sequence of the clone thus obtained is analyzed. Further, the ligase chain reaction method may be applied to the amplification [Wu et al., Genomics, 4, 560–569 (1989)]. Furthermore, a specific mutation in the above-mentioned gent in a sample can be detected by using the allele-specific PCR [Ruano and Kidd, Nucleic Acid Research, 17, 8392 (1989)] or the ARMS method [C. R. Newton et al., Nucleic Acid Research, 17, 2503–2517 (1989)].

Similarly, a point mutation can be detected by the SSCP method [Orita et al., Proc. Natl. Acad. Sic. USA, 86, 2766–2770 (1989); and Genomics, 5, 874–879 (1989)] or the RNase-protection method with the use of probes containing the DNA sequence thus selected or an RNA sequence originating therein. By using these probes, a mutation in the above-mentioned gene in a sample can be detected by the Southern hybridization method or an abnormality in the expression level of this gene in a sample can be examined by the Northern hybridization method.

*Escherichia coli* DH5αF'/pAB1, pFL2 and pCE9 each carrying a plasmid containing the cDNA of this tumor suppressor gene were deposited with National Institute of Bioscience and Human-Technology, Agency of Industrial Science and Technology, Ministry of International Trade and Industry under accession numbers FERM P-14127, 14128 and 14129, respectively, on Feb. 8, 1994, and they were changed to International deposition under accession numbers FERM BP-4923, 4924 and 4925, respectively, on Dec. 9, 1994.

The DNA of the present invention has a structure homologous with those of transcriptional factors, and originates in the most restricted commonly deleted region on chromosome 11 in MEN 1-associated tumors. Therefore, it is expected that the DNA of the present invention may be a novel tumor suppressor gene. The DNA may be used as a tool in gene therapy. Further, a fragment of the DNA may be used in the gene analysis of the DNA and in the diagnosis of diseases to which the DNA relates.

The polypeptide coded for by the DNA according to the present invention may be used as a reagent for investigations and used for preparing an antibody. The antibody may be used in the qualitative or quantitative analysis of the polypeptide in a biological sample. Thus, it is expected that the antibody may be useful as a novel diagnostic drug.

EXAMPLES

To further illustrate the present invention in greater detail and in particular, the following Examples will be given.

EXAMPLE 1

Isolation and Linkage Analysis of Cosmid Clones Specific for Chromosome 11

Figure 1:
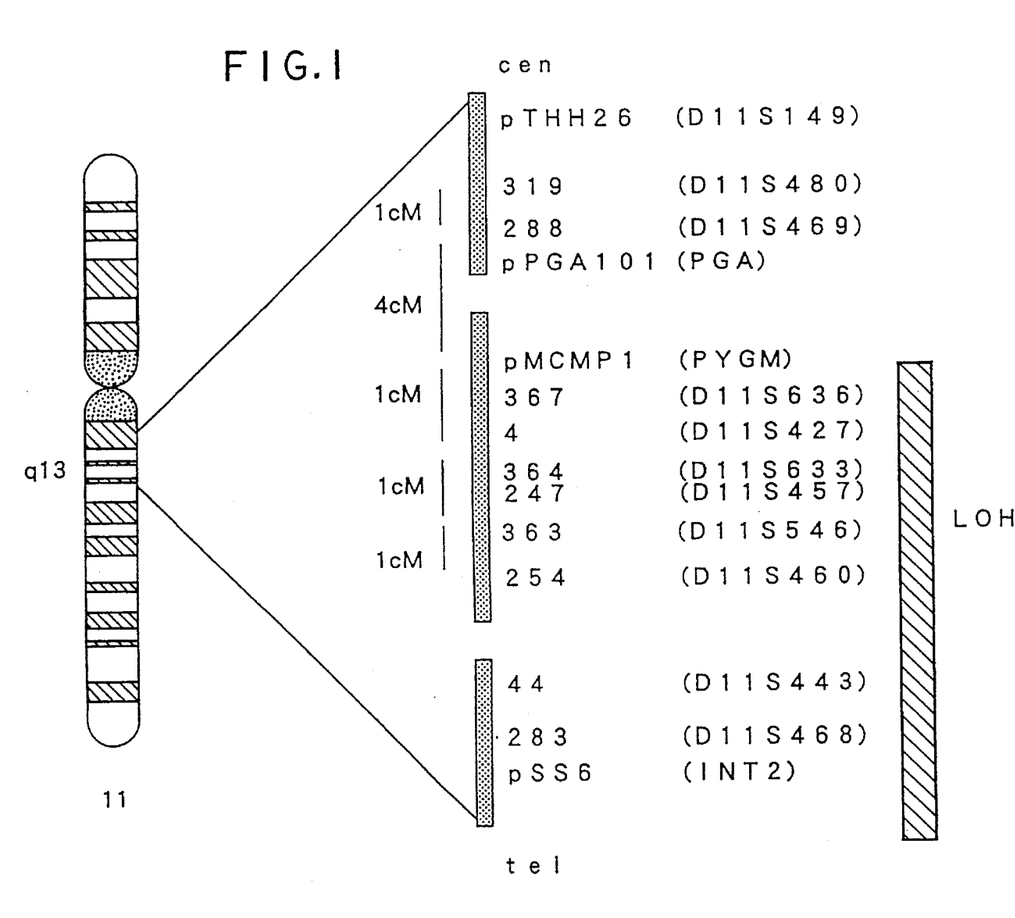
FIG. 1 is a diagram showing the restriction of the region in which the MEN1 gene exists by the linkage analysis and the LOH analysis.

At the early stage of studies, it was reported, based on the linkage with a PYGM (muscle glycogen phosphorylase gene) marker, that a gone participating in the onset of MEN1 existed in the long arm of chromosome 11 [Larrson et al., Nature, 332, 85–87 (1988)]. Subsequently, it was reported that it existed in a region of 12cM located between D11S149 marker and INT2 marker of 11q13 [Nakamura et al., Am. J. Hum. Genet., 44, 751–755 (1989)]. We prepared a cosmid library from a Chinese hamster/human hybrid cell line containing a single human chromosome 11 and screened cosmid clones containing a part of the human chromosomal DNA with the use of a whole human DNA as a probe [Tokino et al., Am. J. Hum. Genet., 48, 258–268 (1991); and Tanigami et al., Am. J. Hum. Genet., 50, 56–64 (1992)]. Then, these clones were tested by hybridization with a hybrid cell line panel containing a part of human chromosome 11 [Tanigami et al., Am. J. Hum. Genet., 50, 56–64 (1992)] and were mapped on the chromosome through the fluorescent in-situ hybridization (FISH) method [Hori et al., Genomics, 13, 129–133 (1992)]. By effecting the linkage analysis with the use of the cosmid markers whereby RFLP could be detected, the location of the MEN1 gene was restricted to a region of 8cM between D11S480 (cCI11-319) and D11S546 (cCI11-363) on q13 of chromosome 11 [Fujimori et al., Am. J. Hum. Genet., 50, 399–403 (1992)] (see FIG. 1).

EXAMPLE 2

Preparation of Deletion Map of Chromosome 11 in MEN1-Associated Tumors

On the other hand, investigations on the loss of heterozygosity (LOH) of the chromosome 11 in MEN1-associated tumors have also suggested that the tumor suppressor gene exists in the above-mentioned region [Friedman et al., N. Engl. J. Med., 321, 213–218 (1989); Thakker et al., N. Engl. J. Med., 321, 218–224 (1989); and Bale et al., Cancer Res., 51, 1154–1157 (1991)]. It has been further pointed out by the mapping of the deleted region on chromosome 11q in these tumors that the MEN1 gene exists in the telomere side of PYGM [Bystroen et al., Proc. Nat. Acad. Sci. USA, 87, 1968–1972 (1990)]. The results of the examination on LOH are arranged together with the results of the linkage analysis and it is thus considered that the MEN1 gene exists in a region of about 3 cM between PYGM and D11S546 (see FIG. 1).

EXAMPLE 3

Preparation of Physical Map of 11q18 Region

We cleaved human genomic DNA with 8 restriction enzymes each having a rare breakage point. After separating DNA fragments by pulse field gel electrophoresis, Southern blotting analysis was carried out by using more than 50 cosmid clones existing in 11q13 as probes. Thus, the relationship in locations among the cosmid clones has been clarified depending upon the capability of each clone of being hybridized with a common genomic DNA fragment. As a result, it has been found out that cCI11-4, cCI11-367, cCI11-364, cCI11-247, cCI11-363, cCI11-254 and PYGM can be hybridized with genomic DNA fragments relating to one another and thus they are located within a range of about 1 Mb in the telomere side of PYGM [Tanigami et al., Genomics, 13, 21–24 (1992)]. It has been suggested that PYGM and cCI11-4, among these cosmid clones, are markers closest to the MEN1 gene (lod values: 5.03 and 5.13) [Fujimori et al., Am. J. Hum. Genet., 50, 399–403 (1992)]. Based on the results of the mapping of the breakage points with restriction enzymes in YAC clones 1908F2 and 199A7 isolated by using PYGM as a probe, it has been clarified that cCI11-367, among the 6 cosmid clones as described above, is also close to PYGM.

EXAMPLE 4

Isolation of Exon Sequence from 11q13 Region

As described above, cCI11-4 and cCI11-367 are cosmid clones which are closest to the MEN1 gene. Thus, an attempt was made to isolate exons from these 2 cosmid clones by the exon trapping method [Buckler, A., et al., Proc. Natl. Acad. Sci. USA, 88, 4005–4009 (1991)]. The cosmid DNA was cleaved with BglII or BamHI, or both of these enzymes, and the fragment thus obtained was linked to the BamHI site of an exon splicing vector pSPL1. Transfection into COS-7 cells and isolation of exon sequences by the reverse transcription PCR (RT-PCR) were effected each in accordance with the procedure described in the original paper. Consequently, 3 exon sequences originating in cCI11-367 were obtained and named respectively s367E1, s367E2 and s367E4. These exon sequences were respectively in sizes of 147 bp, 76 bp and 129 bp.

EXAMPLE 5

Isolation of Full-Length cDNA

Figure 2:
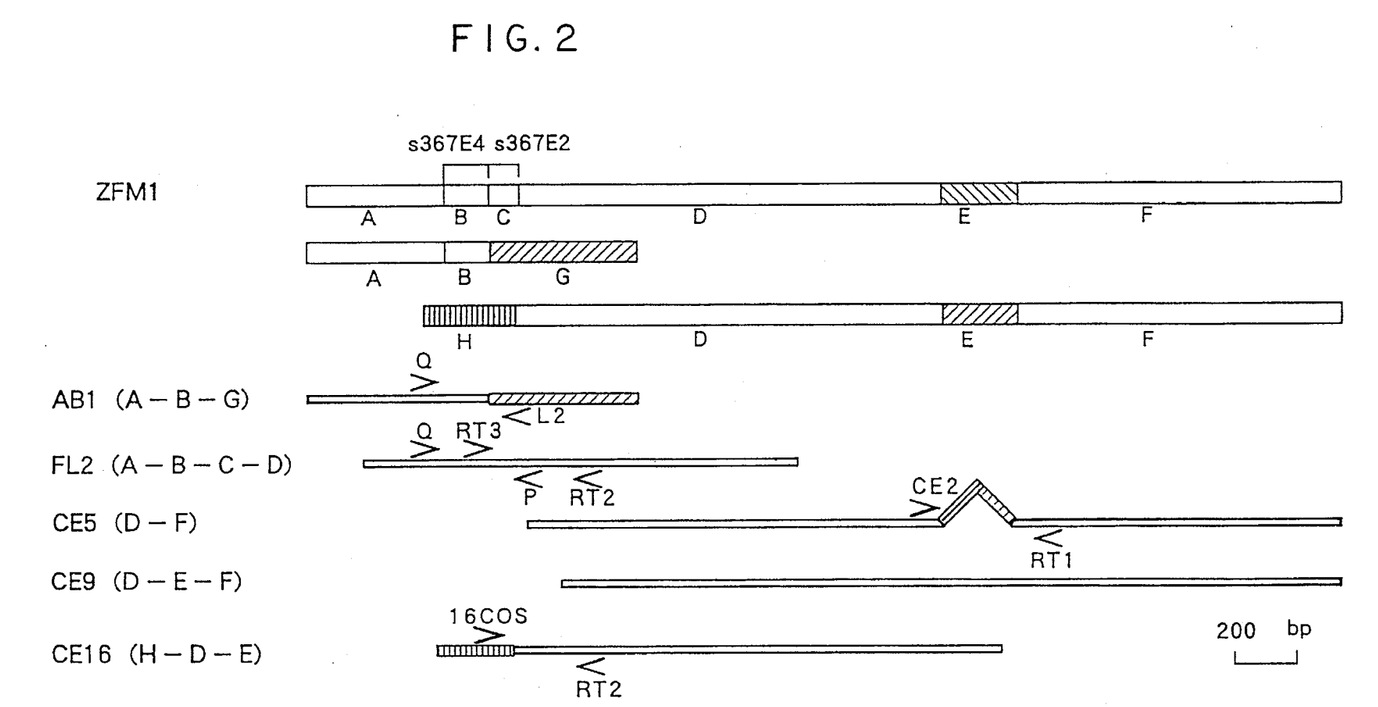
FIG. 2 is a diagram showing cDNA clones which overlap one another and the domain structure of ZFM1 cDNA derived therefrom.

By using s367E4 (i.e., one of the exon sequences obtained in the above Example 4) as a probe, a human cortical cDNA library was screened. Thus, a clone AB1 carrying a cDNA insert of 1 kb was obtained. With the use of this clone AB1 as a probe, further, a cDNA clone FL2 was obtained from a human fetal liver cDNA library while cDNA clones CE5, CE9 and CE16 were obtained from a human cerebellar cDNA library. Then, it was confirmed that each of these clones could be hybridized with the original cosmid clone cCI11-367 and mapped on the chromosome 11q13 with a hybrid cell line panel. A sequence constructed by overlapping these cDNA clones with one another at the common parts corresponded to ZFM1 cDNA of 3200 bp (SEQ ID NO:1). This ZFM1 cDNA contained an open reading frame (ORF) of 1869 bp which corresponded to a sequence of base Nos. 383 to 2251 in SEQ ID NO:1. Based on the information as will be described hereinbelow, it has been proved that the sequence of SEQ ID NO: 1 and that of each clone can be regarded as being composed of 6 domains A (base Nos. 1 to 413 in SEQ ID NO:1), B (base Nos. 414 to 542 in SEQ ID NO:1), C (base Nos. 543 to 618 in SEQ ID NO:1), D (base Nos. 619 to 1964 in SEQ ID NO:1), E (base Nos. 1965 to 2218 in SEQ ID NO:1) and F (base Nos. 2219 to 3200 in SEQ ID NO:1) and domains G and H which are completely different therefrom. Namely, the exon sequences s367E2 and s367E4 obtained in the above Example 4 corresponded respectively to the domains C and B. The cDNA clone CE5 lacked a domain E consisting of 254 base pairs corresponding to a sequence of base Nos. 1965 to 2218 in SEQ ID NO:1, which may be due to an alternative splicing. The cDNA clone AB1 contained domains A and B and the different one G but not the domains C, D, E and F. The cDNA clone CE16 consisted of the domains D and E and the different one It (see FIG. 2).

EXAMPLE 6

Figure 3:
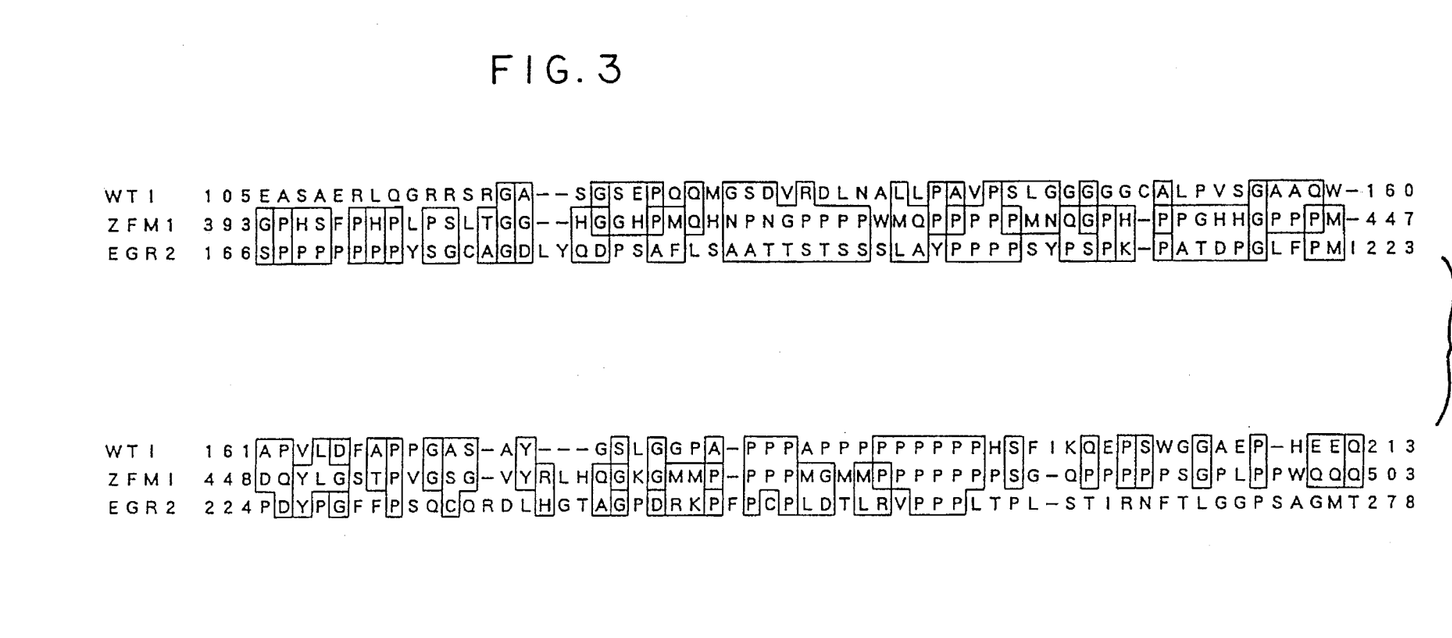
FIG. 3 is a diagram showing the homology of the ZFM1 protein with WT1 or EGR2.

Characteristics of the Structure of the Protein Coded for by the Tumor Suppressor Gene A protein coded for by ZFM1 cDNA consisted of 623 amino acid residues and had a nuclear localizing signal containing basic amino acids in the N-terminal side. Further, a sequence C-X2-C-X4-H-X4-C (amino acid Nos. 279–292) had characteristics of a zinc finger motif existing in a DNA binding protein. 118 proline residues were contained in this ZFM1 protein. In particular, 69 proline residues were contained in a region of amino acid Nos. 420 to 623 thereof. The sequence of this region showed high homologies with Wilms' tumor suppressor gene product (WT1) [Gessler et al., Nature, 343, 774–778 (1990)] and early growth response 2 (EGR2) protein as a transcriptional factor (27.3% and 24.0%, respectively) (see FIG. 3). WT1 is a transcription factor having a Kruppel-like zinc finger motif [Rosenberg et al., Nature, 319, 336–339 (1986)]. EGR2 is a human homologue of an early growth response gene Krox-20 [Chavier et al., EMBO J. 7, 29–35 (1988)] which is expressed at the G0-G1 junction in the cell cycle of cultured mouse cells and it is also a transcriptional factor [Joseph et al., Proc. Natl. Acad. Sci. USA, 85, 7164–7168 (1988)]. The ZFM1 protein further had 7 proline repetitive sequences (each consisting of at least 4 proline residues located continuously) in the C-terminal side. One of these repetitive sequences followed a glutamine repetitive sequence and thus formed a structure which was almost the same as that of the hinge domain of a mineralocorticoid receptor [Arriza et al., Science, 237, 268–275 (1987)]. Such a hinge structure is essentially required in the communication between a hormone binding domain and a DNA binding domain [Krust et al., EMBO J., 5, 891–897 (1986); and Giguere et al., Cell, 46, 645–652 (1986)]. Further, mRNAs of a number of types originating in the ZFM1 gene were expressed in hormone-producing organs such as pancreas, thyroid, adrenal gland and ovarium (see Table 1 in Example 8).

These facts indicate that the ZFM1 protein is a tumor suppressor gene which is localized in the nuclei and exerts its function by binding to DNA and thus suppressing the proliferation of cells and that ZFM1 is a gent which participates in the onset of MEN1.

EXAMPLE 7

Structure of Genomic Gene

Figure 4:
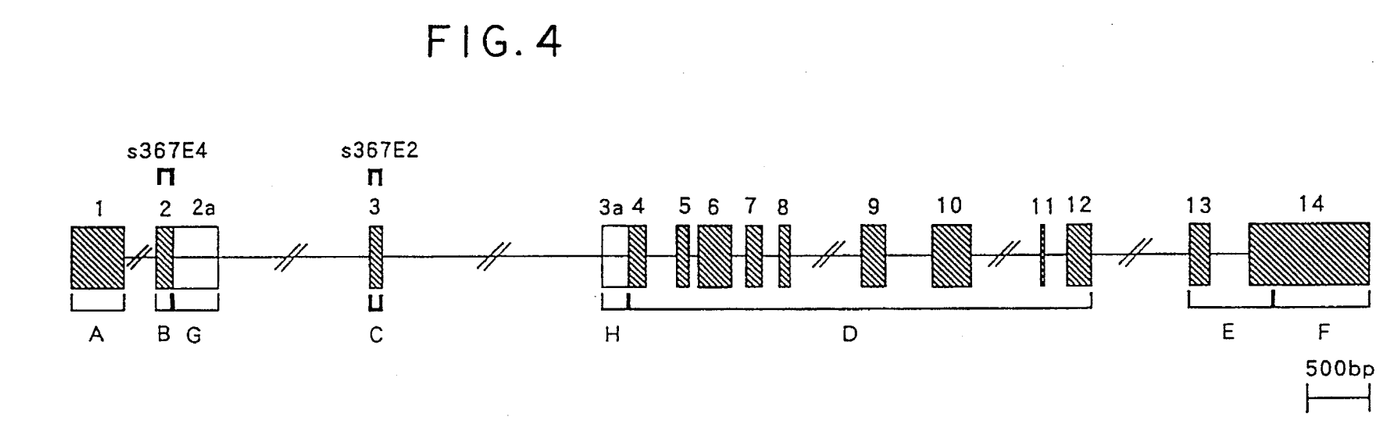
FIG. 4 is a diagram showing the constitution of exerts of the ZFM1 gene. The exons are represented by 1 to 14. The domains observed in cDNA are represented by A to H.

Based on the cosmid clone containing the ZFM1 gone, the genomic structure of the ZFM1 gene was determined. The ZFM1 gene existed over a region of about 20 kb in the genomic DNA and consisted of 14 exons (see FIG. 4). As FIG. 4 shows, it has been revealed that these exons (Nos. 1 to 14) and the domains A to H described in the above Example 6 relate to each other as follows: domain A=exon 1, domain B=exon 2, domain C=exon 3, domain D=exon 4, 5, 6, 7, 8, 9, 10, 11 and 12, domain E=exon 13 and a part of exon 14, domain F=a part of exon 14, domain G=exon 2a, and domain H=exon 3a.

The sequence of SEQ ID NO: 1 contains all of these 14 exons except the exons 2a and 3a. The sequence of the cDNA clone CE5 consisting of the domains D–F lacks in the domain E corresponding to the exon 13 and a part of the exon 14. On the other hand, the domain G of the cDNA clone AB1 consisting of the domains A-B-G is coded for by the exon 2a which directly follows the exon 2 coding for the domain B. Also, the domain H of the cDNA clone CE16 consisting of the domains H-D-E is coded for by the exon 3a which is located immediately before the exon 4 coding for the domain D.

EXAMPLE 8

Expression of ZFM1 Gene in Human Tissues

By using an insert of the cDNA clone FL2 as a probe, mRNAs of various tissues were analyzed by the Northern blotting method. As a result, the expressions of ZFM1mRNAs of 3.3 kb and 2.7 kb were observed in all of these tissues. It is considered that the larger mRNA corresponds to the full length cDNA containing the domains A-B-C-D-E-F, while the smaller mRNA corresponds to one containing the domain H instead of the domains A-B-C (see FIG. 2). To examine the expression of the ZFM1 gene in greater detail, the reverse transcription PCR (RT-PCR) analysis was effected by extracting RNAs from various human tissues and using primer sets (see the arrow heads in FIG. 2) specific for the respective domains. As a result, the expressions of ZFM1 mRNAs of various types, which were thought to be due to differences in splicing, were observed over a wide range of tissues. The expressions of 3 mRNAs having structures of A-B-C-D, A-B-G and H-D (see FIG. 2) were observed in nearly all tissues, though the expression yields differed from one another. In contrast, the expression of a mRNA having the domain E was restricted to heart, pancreas, thyroid and ovarium (see Table 1).

TABLE 1

| Domains | Tissue-specific expression of ZFM1 | | | | | | | | | | |
|---|---|---|---|---|---|---|---|---|---|---|---|
| | cerebrum | cerebellum | heart | lung | liver | pancreas | colon | kidney | thyroid | adrenal gland | ovarium |
| ABCD | + | − | + | ++ | + | +++ | ++ | + | +++ | + | +++ |
| ABG | − | − | + | +++ | + | +++ | + | + | ++++ | ++ | +++ |
| HD | − | − | + | ++ | + | +++ | + | + | +++ | ++ | +++ |
| DEF | − | − | + | − | − | + | − | − | + | − | + |
| DF | − | + | ++ | + | + | +++ | + | + | +++ | ++ | ++ |

What we claim is:

1. An isolated DNA fragment comprising the full structure or a part of the DNA represented by SEQ ID NO: 1, wherein said part of the DNA comprises a base sequence of at least 10 contiguous bases from the DNA represented by SEQ ID NO: 1.

2. The isolated DNA fragment of claim 1, wherein said part of the DNA comprises a base sequence of from 10 to 30 contiguous bases from the DNA represented by SEQ ID NO:1.

3. The isolated DNA fragment of claim 1, wherein said part of the DNA comprises a base sequence of at least 15 contiguous bases from the DNA represented by SEQ ID NO:1.

4. The isolated DNA fragment of claim 3, wherein said part of the DNA comprises a base sequence of from 15–25 contiguous bases from the DNA represented by SEQ ID NO:1.

5. The isolated DNA fragment of claim 1, wherein said part of the DNA comprises a base sequence of at least 20 contiguous bases from the DNA represented by SEQ ID NO:1.

6. The isolated DNA fragment of claim 1, comprising the full base sequence of the DNA represented by SEQ ID NO:1.

7. A transformant transformed by a plasmid having, integrated therein, the full structure or the DNA represented by SEQ ID NO:1 which can be expressed therein.

* * * * *

UNITED STATES PATENT AND TRADEMARK OFFICE
CERTIFICATE OF CORRECTION

PATENT NO. : 5 559 023
DATED : September 24, 1996
INVENTOR(S) : Yusuke NAKAMURA et al.

It is certified that error appears in the above-indentified patent and that said Letters Patent is hereby corrected as shown below:

Column 18, line 33; change "structure or the" to ---structure of the---.

Signed and Sealed this

Fourth Day of March, 1997

Attest:

BRUCE LEHMAN

Attesting Officer

Commissioner of Patents and Trademarks